United States Patent
Kawai et al.

(10) Patent No.: US 7,045,597 B2
(45) Date of Patent: May 16, 2006

(54) MAST CELL SURFACE ANTIGEN, DNA THEREOF, AND ANTIBODY AGAINST THE ANTIGEN

(75) Inventors: Makoto Kawai, Nagoya (JP); Tadashi Okada, Nisshin (JP); Fukiko Atsumi, Nagoya (JP); Masao Shibata, Ina (JP); Motoki Kuhara, Ina (JP)

(73) Assignee: Medical & Biological Laboratories Co., Ltd., Nagoya (JP)

( * ) Notice: Subject to any disclaimer, the term of this patent is extended or adjusted under 35 U.S.C. 154(b) by 56 days.

(21) Appl. No.: 10/250,644

(22) PCT Filed: Jan. 4, 2001

(86) PCT No.: PCT/JP01/00005

§ 371 (c)(1),
(2), (4) Date: Nov. 4, 2003

(87) PCT Pub. No.: WO02/055696

PCT Pub. Date: Jul. 18, 2002

(65) Prior Publication Data

US 2004/0152870 A1     Aug. 5, 2004

Related U.S. Application Data

(63) Continuation-in-part of application No. 09/229,932, filed on Jan. 13, 1999, now Pat. No. 6,255,107.

(51) Int. Cl.
*C07K 14/435* (2006.01)
*A61K 39/00* (2006.01)

(52) U.S. Cl. .................................. 530/350; 424/185.1

(58) Field of Classification Search ................ 530/350
See application file for complete search history.

(56) References Cited

FOREIGN PATENT DOCUMENTS

EP        943625 A1       9/1999

OTHER PUBLICATIONS

Monaco, C. et al., "Molecular Cloning and Characterization of LOH11CR2A, a New Gene wihin a Refined Minimal Region of LOH at 11q23", 1997, Genomics, vol. 46: pp. 217-222.*
Martin, E. et al. "The BCSC-1 locus at chromosome 11q23-q24 is a candidate tumor suppressor gene", 2003, PNAS, vol. 100: pp. 11517-11522.*

* cited by examiner

*Primary Examiner*—Scott D. Priebe
*Assistant Examiner*—Michael Burkhart
(74) *Attorney, Agent, or Firm*—Davis & Bujold, P.L.L.C.

(57) ABSTRACT

A mast cell surface antigen, DNA thereof and an antibody against the antigen are provided. The amino acid sequence of this mast cell surface antigen is the translation of the coding region of its DNA. The base sequence of this DNA has been clarified in the following manner. Namely, mast cells obtained by incubating cord blood monocular cells are co-incubated with primary culture of fibroblasts to give connective tissue type mast cells (MC-TC). Then mRNA is extracted from this MC-TC cell extraction and a cDNA library is constructed therefrom. Immunological screening is carried out with the use of anti-MC-TC antiserum and the base sequence of the positive clone thus obtained is identified. Owing to the clarification of the amino acid sequence of this mast cell antigen, it becomes possible to reveal the role of mast cells in the pathology of allergic diseases and thus an antibody against mast cells can be easily obtained.

1 Claim, 3 Drawing Sheets

FIG. 2

<210> 8
<211> 2551
<212> DNA
<213> human
<400> 2

```
gcacaccatg gtgcacttct gtggcctact caccctccac cgggagccag tgccgctgaa   60
gagtatctct gtgagcgtga acatttacga gtttgtggct ggtgtgtctg caactttgaa  120
ctacgagaat gaggagaaag ttcctttgga ggccttcttt gtgttcccca tggatgaaga  180
ctctgctgtt tacagctttg aggccttggt ggatgggaag aaaattgtag cagaattaca  240
agacaagatg aaggcccgca ccaactatga gaaagccatc tcccagggcc accaggcctt  300
cttattggag ggggacagca gctccaggga tgtcttctct tgcaatgtgg gtaacctcca  360
acctgggtcg aaggcggcag tcaccctgaa gtatgtgcag gagctgcctc tggaagcaga  420
tggggctctg cgctttgtgc tcccagctgt cctgaatcct agataccagt tctctgggtc  480
gtctaaggac agttgcctta atgtgaagac tcctatagtc cctgtggagg acctgcccta  540
cacactcagc atggtcgcca ccatagattc ccagcatggc attgagaagg tccaatccaa  600
ctgccccttg agtcctaccg agtacctagg agaggacaag acttctgctc aggtttccct  660
ggctgctgga cacaagtttg atcgggacgt ggaactcctg atttactaca tgaggtgca  720
tacccccagc gtggttttgg agatggggat gcctaacatg aagccaggtc atttgatggg  780
agatccatct gcaatggtga gtttctatcc aaatatccca gaagatcaac catcaaatac  840
ctgtggagag tttatctttc tcatggaccg ctcgggaagt atgcagagcc ccatgagtag  900
ccaggataca tctcgctgcg aatacaggca gccaaggaaa cactgatttt gctgctgaag  960
agtttaccta taggctgtta tttcaacatc tatggatttg gctcttccta tgaggcatgc 1020
tttccggaga gtgtgaagta cactcagcaa acaatggagg aggctctggg gagagtgaag 1080
cttatgcagg ccgacctagg gggcactgaa atcttggcac cactccagaa catttacagg 1140
ggaccctcca tcccaggcca cccccctacag cttttttgtct ttacagatgg agaagttaca 1200
gacacgttta gtgtaattaa agaagttagg atcaacagac agaaacacag gtgtttctca 1260
tttggtattg gagaaggcac ctccaccagc ctaataaaag gtattgcccg ggcatcaggg 1320
ggcacctcag aatttatcac aggcaaagac aggatgcagt ccaaggctct caggactctg 1380
aaacgctctc tgcagcctgt ggtagaggat gtctctctga gctggcatttt gcctcctggt 1440
ctgtctgcta aaatgctttc cccagaacag actgtcatct ttaggggtca gagattaatc 1500
agctatgccc agctgaccgg gaggatgcca gcagcagaga caacaggaga gtatgcctc 1560
aaatatacac tccagggcaa gactttgag gataaggtga catttcctct acaacccaag 1620
cctgatgtca acctcaccat tcaccgcctt gctgccaagt ccttgctcca gaccaaggac 1680
atgggcctca gggagactcc agcaagtgat aaaaagatg cattgaacct tagccttgag 1740
tctggtgtca taagctcctt cacagctttc attgctatca ataaggagct caacaagccg 1800
gttcaggggc ctctggctca tagggacgtc ccaaggccaa ttctgttggg tgcttctgcc 1860
ccattgaaga taaaatgcca atcaggtttt cgaaaggcct tacactctga ccgtcctcct 1920
tctgcatctc agcccagagg ggaacttatg tgttataagg ccaagacatt ccagatggac 1980
gattacagtc tctgtgggtt gataagtcac aaggaccagc acagtccagg ctttggagag 2040
aatcaccttg tgcagctgat ttaccaccaa aatgcaaatg gttcctggga tctgaatgaa 2100
gatctagcca agatcctagg tatgagtttg gaagaaataa tggctgcaca gcctgccgag 2160
cttgtggatt cctcaggctg gccaccatc ctggccgtga tctggctgca cagcaatggt 2220
aaggacttga agtgtgaatg ggagcttctg gaaaggaagg ccgtggcctg gatgcgtgcc 2280
catgcaggct ccaccatgcc ttcggttgtg aaagctgcta ttacttttcct gaagtcatct 2340
gtggatcctg ctatctttgc cttttgaaga taccatccag aaaaagaagt gcctttaatt 2400
tgctactgtc atttcctcta gtatcacttt gctgtgatg atgtgttctt gtgtattata 2460
actctttatt ttttgccata aaagtaaagg atgcttactc cacttcgctt ctctgctcca 2520
ggttcacttt ggatatgatc tttcttttcc c                                2551
```

CONSTRUCTION OF
cDNA EXPRESSION VECTOR BCMGSNeo
CMVp: CYTOMEGALOVIRUS PROMOTOR,
poly(A): POLY(A) SIGNAL,
Intron: SPLICING INTRON,
NeoR: NEOMYCIN-RESISTANT GENE,
AmpR: AMPICILLIN-RESISTANT GENE,
ori: ORIGIN OF REPLICATION

US 7,045,597 B2

MAST CELL SURFACE ANTIGEN, DNA THEREOF, AND ANTIBODY AGAINST THE ANTIGEN

This application is a continuation in-part of Ser. No. 09/229,932 filed Jan. 13, 1999, now U.S. Pat. No. 6,255,107.

TECHNICAL FIELD OF THE INVENTION

This invention relates to a mast cell surface antigen, DNA thereof, and antibody against the antigen.

BACKGROUND OF THE INVENTION

Allergic diseases, such as bronchial asthma or allergic rhinitis, are induced as follows: firstly, antigen-specific IgE production is induced, and then, from mast cells, basophils and the like, activated by the induced IgE, various chemical mediators such as histamine, eosinophil chemotactic factor in allergy (ECF-A), leukotrienes, platelet-activating factor (PAF) and thromboxane are produced and released. Specifically in tissues, the mast cells release these chemical mediators, and therefore play an important role in development of allergic diseases.

Human mast cells are differentiated into tryptase positive cell (MC-T) and both tryptase and chymase positive cells (MC-TC), according to the granule content of proteolytic enzyme in the mast cells. MC-T are mainly distributed in the lung tissues and the gastrointestinal tract mucosa, whereas MC-TC are distributed in the skin tissues. These mast cells, unlike cells of other leukocytes, leave bone marrow for the peripheral environment as pluripotent stem cells, and differentiate into MC-T or MC-TC, followed by adhesion to either lung or skin fibroblasts. Since it is believed that such mast cells play a major role in development of allergic diseases, it is necessary to specifically detect and separate the mast cells in order to clarify the physiological functions of the mast cells.

However, heretofore, no cell surface antigen specific to the mast cells has been known. Since the antibody against the cell surface antigen specific to the mast cells will allow us to specifically remove or eliminate the mast cells, identification of the cell surface antigen specific to the mast cells has an important meaning not only in clarification of the underlying cause of allergic diseases but in treatment thereof.

An object of the present invention, which was made to solve the above problem, is to provide a mast cell surface antigen, DNA thereof, and an antibody against the antigen.

DISCLOSURE OF THE INVENTION

The mast cell surface antigen comprises an amino acid sequence listed in SEQ ID NO. 1, or a substantially identical amino acid sequence. This amino acid sequence is a translation of the coding region of DNA of the mast cell surface antigen. The base sequence of the DNA of the mast cell surface antigen has been clarified in the following manner. Namely, as explained in detail in an embodiment section, after mast cells are obtained from cord blood monocular cells, mRNA is extracted from cell extraction of these mast cells, and a cDNA library is constructed from the mRNA. Immunological screening of the cDNA library is carried out using the antiserum, and the base sequence of the positive clone thus obtained is identified by means of a DNA sequencer. In the base sequence listed in SEQ ID NO. 2, a sequence of 36–38, namely ATG, is the initiation codon, and a sequence of 2394–2396, namely, TGA, is the termination codon. In other words, a sequence of 36–2396 is the coding region, and the base sequence in the range codes the amino acid sequence listed in SEQ ID NO. 1. Identification of the amino acid sequence of this mast cell antigen allows us to clarify the role of the mast cells in development of allergic diseases, and thus to obtain the antigen which specifically reacts to the mast cells.

An antibody against the mast cell surface antigen can be obtained in the following steps, for example. Firstly, the mast cell antigen comprising the amino acid sequence listed in SEQ ID NO. 1 is injected to a mammal (except human) for immunization, and fused cells are prepared by fusing the antibody producing cells obtained from the immunized mammal with myeloma cells. Then, from the fused cells, a clone which produces an antibody that reacts with the mast cell surface antigen is selected and cultured, and the supernatant of the culture is purified. The antibody allows us to specifically remove or eliminate the mast cells, and thus to treat allergic diseases. In short, this antibody is expected to work as antiallergic agent.

Cells that produce this antibody can be obtained in the following steps, for example. Firstly, the mast cell antigen comprising the amino acid sequence listed in SEQ ID NO. 1 is injected to a mammal (except human) for immunization, and fused cells are prepared by fusing the antibody producing cells obtained from the immunized mammal with myeloma cells. Then, from the fused cells, a clone which produces an antibody that reacts with the mast cell surface antigen is selectively cultured.

BRIEF DESCRIPTION OF THE DRAWINGS

FIG. 2 is an explanatory view showing the base sequence of Bcsc-1 (SEQ ID NO: 8)

BEST MODE FOR CARRYING OUT THE INVENTION

[1] Culture of MC-TC

Cord blood treated with heparin was layered over the Ficoll Hypaque solution (specific gravity: 1.077, Sigma Inc.), centrifuged at 300×g for 30 minutes at room temperature to separate the mononuclear cells, which were then suspended in RPMI1640 medium (Nissui Seiyaku) containing 10% of FBS (Gibco BRL), 50 ìM of 2-mercaptoethanol, 4 mM of L-glutamine, 100 U/ml of penicillin and 50 ìg/ml of streptomycin. The concentration of the mononuclear cells in the suspension was adjusted to $5 \times 10^6$/ml, and the suspension was poured into a collagen coated culture dish (Iwaki Glass) having a diameter of 10 cm, and, added with SCF (100 ng/ml, PeproTech Inc.) and IL-6 (50 ng/ml, PeproTech Inc.), cultured for 2 weeks to obtain two-week cultured cells containing neutrophils, lymphocytes, macrophages, basophils and precursor cells of mast cell. SCF is a factor participating in differentiation and proliferation of mast cells expressed on fibroblasts. It is an abbreviation for stem cell factor.

The cord blood mononuclear cells obtained in the above were cultured in the presence of 100 ng/ml of SCF and 50 ng/ml of IL-6 for 6 weeks, and when the human mast cells became predominant, that is, when the number of human mast cells reached the order of $10^6$, the mast cells were further cocultured with a primary culture of human fibroblasts. Specifically, the human mast cells were transferred to a monolayer of human fibroblasts from either skin or lung tissues, and cultured for 2 months in the presence of 50 ng/ml SCF.

Figure 1:
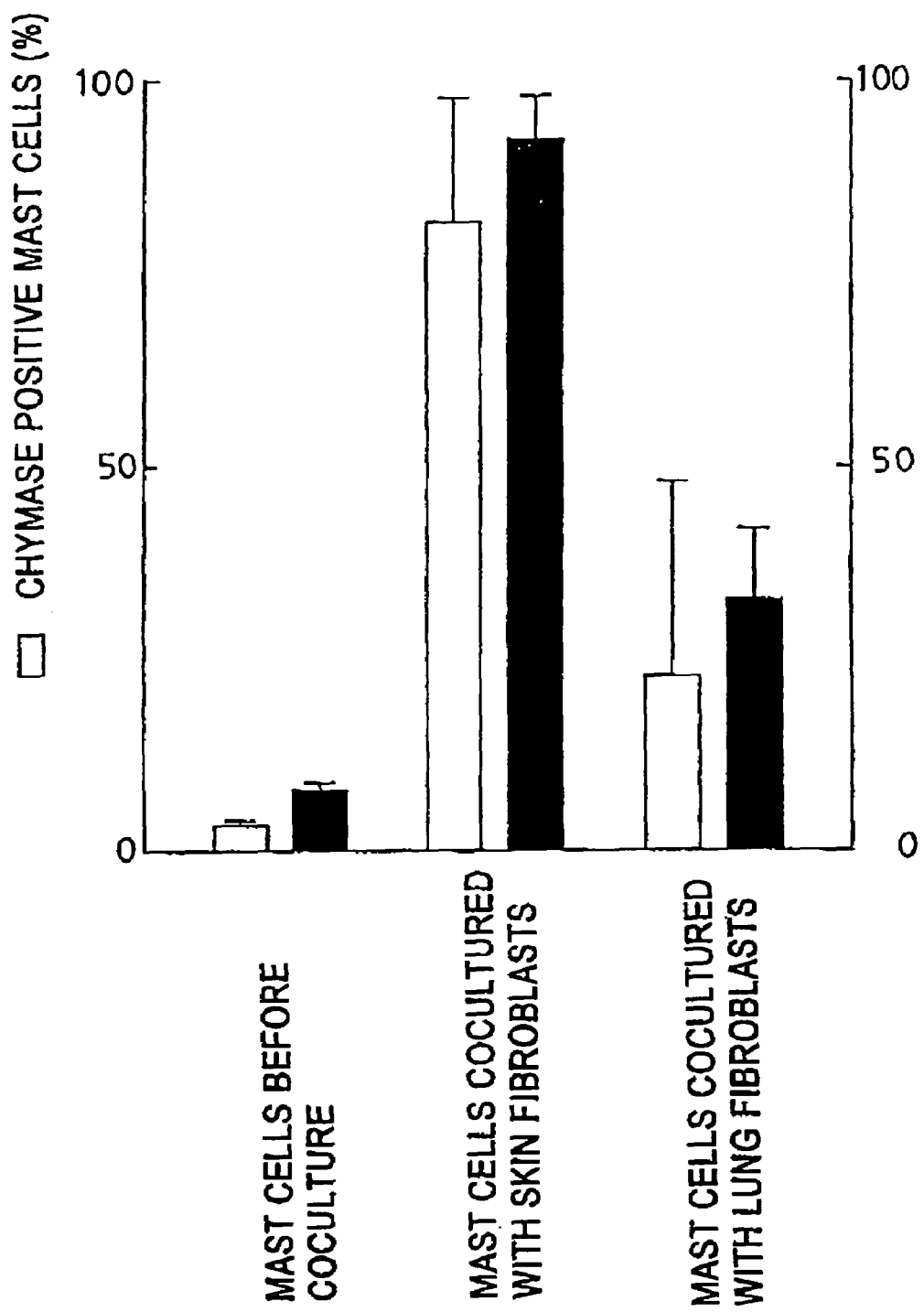
FIG. 1 is a graph showing the ratio of chymase positive mast cells and measured values of tryptase concentration for the mast cells before and after coculture.

The ratio of chymase positive mast cells and the concentration of tryptase were measured for the mast cells before and after the coculture. The result is shown in FIG. 1. FIG. 1 shows that before the coculture of mast cells, i.e. for the human mast cells cultured for 10–16 weeks in the presence of SCF and IL-6 (the left end of the graph in FIG. 1), the ratio of chymase positive cells and the concentration of tryptase were both very low, whereas those for the human mast cells after cocultured with human fibroblasts for 6–8 weeks (the center of the graph in FIG. 1) and those for the human mast cells cocultured with lung fibroblasts (the right end of the graph in FIG. 1) showed remarkable increases, especially for the human mast cells cocultured with skin fibroblasts.

Staining was performed to the mast cells cultured for 15 weeks in the presence of SCF and IL-6 and the mast cells cocultured with skin fibroblasts for 2 months after having been cultured for 6 weeks, using antibodies against tryptase and those against chymase. As a result, in case of staining against tryptase, it was confirmed that both types of mast cells were wholly stained, whereas in case of staining against chymase, it was confirmed that most cells cocultured with fibroblast were stained but cells which were not cocultured were only partly stained. The results show that MC-T is differentiated into MC-TC by the coculture.

As described above, connective tissue type-human mast cells, or MC-TC, were obtained by culturing cord blood monocular cells in the presence of SCF and IL-6 and subsequently coculturing them with the primary culture of human skin fibroblasts.

[2] Preparation of mRNA

According to the manual of "Quick-Prep Micro mRNA Purification Kit" of Pharmacia, poly(A)+mRNA was extracted from the cell extraction of the above MC-TC in the following steps.

$2 \times 10^6$ of MC-TC was centrifuged and washed with PBS twice, added with 400 ìL of elution buffer accompanying the aforementioned kit, stirred well by a vortex mixer (rotary beater), further added with 800 ìL of elution buffer and stirred by the vortex mixer. The solution obtained was transferred into an assist tube (Assist) made of polypropyrene, and centrifuged at 14,000 rpm for 5 minutes to separate the precipitate.

1 mL of oligo dT cellulose was centrifuged at 14,000 rpm to separate the supernatant.

The oligo dT cellulose in 2) was added to the cell extraction in 1), and the solution was well mixed by inverting the assist tube for 3 minutes, centrifuged at 14,000 rpm for 5 seconds to separate the supernatant, which was then washed with 1 mL of high salt concentration buffer 5 times and then in low salt concentration buffer 2 times.

The precipitate was suspended in 300 ìL of low salt concentration buffer, put in a microspin column accompanying the aforementioned kit, which was centrifuged for 5 seconds, and washed with 500 ìL of low salt concentration buffer 3 times.

200 ìL of elution buffer warmed up to 65° C. was added to the column, and 10 ìL of glycogen solution and 400 ìL of potassium acetate solution were further added. After 1 mL of 95% ethanol was added, the column was centrifuged at 14,000 rpm for 1 hour at 4° C., and dried under reduced pressure.

[3] Construction of cDNA Library

According to the manual of "Zap-cDNA synthesis kit" of Stratagene, a cDNA library was constructed from mRNA obtained in the above [2]. Size fractionation was carried out using CL-2B gel accompanying this kit.

[4] Immunological Screening

A phage solution of the cDNA library constructed in the above [3] was diluted with SM buffer (containing 50 mM of Tris-HCl (pH7.5), 100 mM of NaCl, 10 mM of $MgSO_4 \cdot H_2O$, and 0.01% gelatin), to give a phage concentration of $2.5–4 \times 10^5$ pfu/mL. This solution was dispensed per 100 ìL to 10 centrifuging tubes. Added with 500 ìL of overnight culture solution of *Escherichia coli* (XL-1 blue) (which was cultured overnight in 5 mL of NZY medium so as to obtain $O.D._{600}=1.5$), the solution was stirred with a vortex mixer, and incubated at 37° C. for 15 minutes. Further added with 7 mL of soft agarose (which was made to give a concentration of 0.6%, by dissolving agarose gel for electrophoretic migration in a culture medium), the solution was stirred by the vortex mixer, and spread in a 14×10 cm square dish. When the agarose was set, the dish was soaked in 20 mL of IPTG, and with a dried nitrocellulose filter thereon, incubated at 37° C. for 4 hours. For the NZY medium, 5 g of NaCl, 2 g of $MgSO_4 \cdot 7H_2O$, 5 g of yeast extract, and 5 g of NZamine (casein hydrolysate) were dissolved in 1 liter of water, the pH was adjusted to 7.5 with NaOH, the solution added with 15 g agar was sterilized and dissolved in an autoclave.

After the incubation, the filter was removed, and washed with shaking with 300 mL PBS for 15 minutes, which was repeated 2 times. Then, the PBS was discarded. Added with 300 mL of PBS (PBS-SM) containing 0.5% skim milk, the filter was washed with shaking for 1 hour at room temperature for blocking. Added with a rat antiserum (which is an antiserum obtained from a rat which provided its spleen cells for preparation of a later-described hybridoma clone ahMC5C12 (Accession No. FERM BP-6070)) diluted 1:400 in PBS-SM, the filter was washed with shaking for 1 hour at room temperature. The antiserum solution was discarded, and the solution was washed with shaking with PBS plus 0.05% Tween (PBS-T) for 5 minutes at room temperature, which was repeated 4 times. Then, added with 200 mL of peroxydase labeled anti-rat IgG (Medical & Biological Laboratories Co., Ltd.) diluted 1:1000 in PBS-SM, the filter was washed with shaking for 1 hour at room temperature, washed with shaking 4 times with 500 mL of PBS-T, and further twice with 100 mL of PBS.

The filter was drained, soaked in a color substrate solution (solution of 12 mg of diaminobenzidine/25 mL of PBS, added with 50 ìL of 2.5% cobalt chloride and 50 ìL of 2% nickel sulphate), and further added with 80 ìL of 30% hydrogen peroxide solution for color development. Based on the location of color development, associated clones were selected.

[5] Determination of Base Sequence

According to the manual of the aforementioned "Zap-cDNA synthesis kit" of Stratagene, in vivo excision of 2 positive clones obtained by immunological screening from the Uni-ZAP XR vector was carried out. The clones were subcloned in pBluescript phagemid and grown with *Escherichia coli*. The base sequences of the respective clones were determined using ABI PRISM 377 DNA sequencer of Perkin Elmer.

In homology search by BLAST conducted against the database for the obtained base sequences, the base sequence of one clone was approximately coincided with that of tryptase III, and the base sequence of the other clone was approximately coincided with that of a gene named Breast cancer suppressor candidate-1 (Bcsc-1) (FIG. 2). In FIG. 2, SEQ ID NO. 8, a sequence of 1-2552 represents Bcsc-1. BLAST is an abbreviation of Basic Local Alignment Search Tool.

A clone having the approximately identical base sequence to that of tryptase III was determined to have nothing to do with the target cell surface antigen, since tryptase III is a well-known enzyme which exists in mast cell granules. Then, it was determined whether the clone having the approximately identical base sequence to that of Bcsc-1 is the target cell surface protein.

[6] Transfection to BHK Cells

Figure 3:
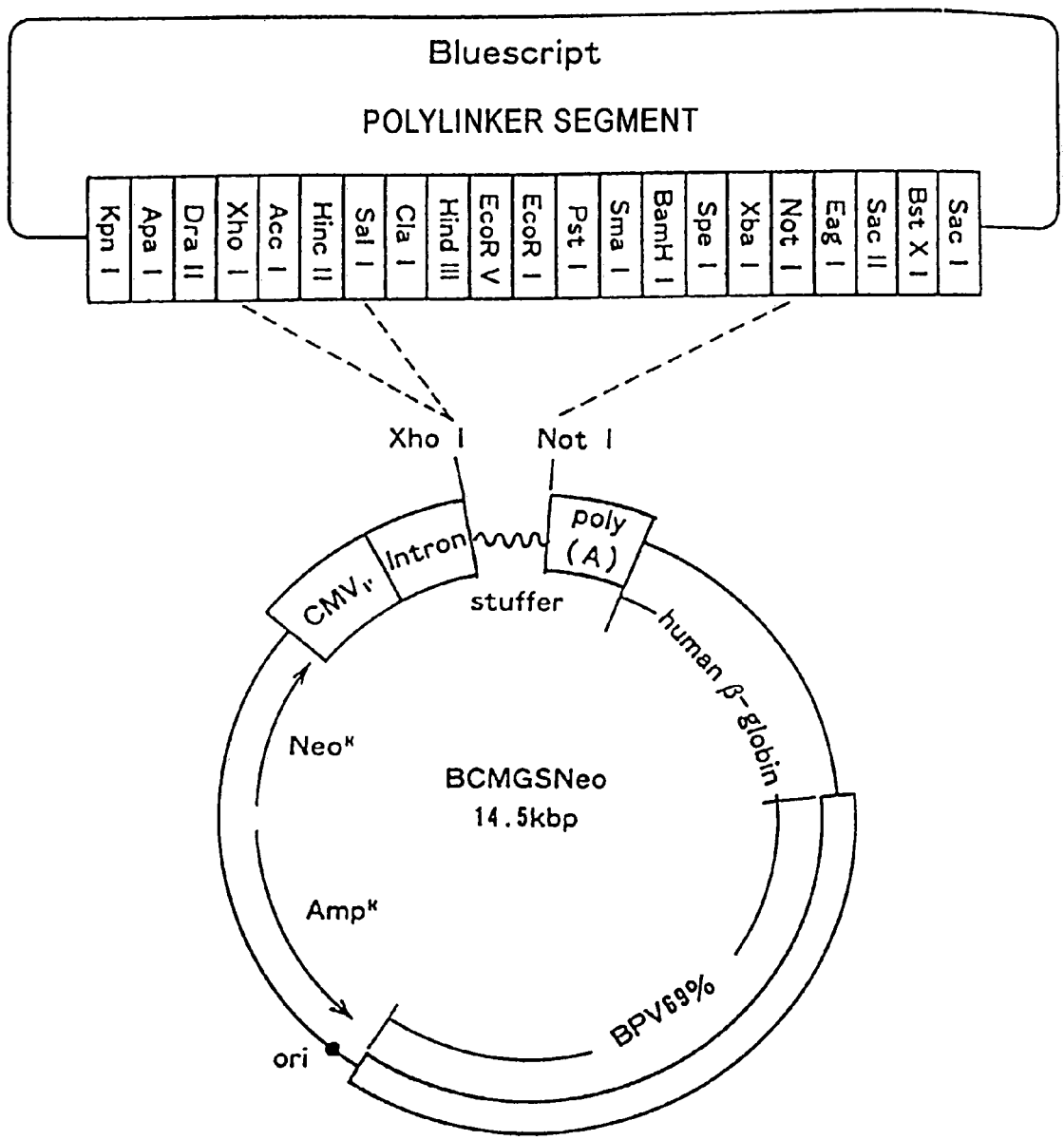
FIG. 3 is an explanatory view showing a construction of a cDNA expression vector BCMGSNeo.

Among the cDNA obtained in the above, the part designated as a region for coding protein of Bcsc-1 stored in the database was inserted to an expression vector which was prepared according to the method of Karasuyama et al. (see FIG. 3; Karasuyama, H. & Melchers, F.: Eur. J. Immunol., 18, 97–104, 1988, Karasuyama, H., Tohyama, N. & Tada, T.: J. Exp. Med., 169, 13–35, 1989, Yagita, H., Nakamura, T., Karasuyama, H. & Okumura, K.,: Proc. Nati. Acad. Sci. USA, 86, 645–649, 1989, Karasuyama, H., Kudo, A. & Melchers, F.: J. Exp. Med., 172, 969–972, 1990). Particularly, in introduction of XhoI and NotI restriction enzyme fragments into Bcsc-1, cagCTCGAGatggaggaggctctgggg (SEQ ID NO. 3) was used as 5' XhoI primer, and tctggat-GCGGCCGCtcaaaggcaaagat (SEQ ID NO. 4) was used as 3' NotI primer. As PCR conditions, the Bcsc-1 was heated at 94° C. for 4 minutes, reacted at 95° C. for 1 minute and 15 seconds, at 60° C. for 1 minute and 10 seconds, and 72° C. for 3 minutes, which was repeated 39 times, and then reacted at 72° C. for 5 minutes. The Bcsc-1 introduced with XhoI and NotI site was treated with XhoI and NotI, and then inserted to BCMGSNeo which was also treated with XhoI and NotI.

The BHK cells were introduced to Bcsc-1 by lipofection and genetically transformed. Namely, the BHK cells were spread in 10% FCS DMEM (Nissui Seiyaku) to give a density of 50–70%, and after cultured overnight, cultured at 37° C. for 2 hours in a fresh medium. The BHK cells were washed 3 times with serum-free DMEM. 100 iL of serum-free DMEM containing 2.5 iL (2.5 ig) of Bcsc-1 introduced BCMGSNeo, and 200 iL of equivalent mixture of 100 iL of serum-free DMEM containing 100 iL of lipofectamin were added to 800 iL of serum-free DMEM, and the BHK cells were cultured at 37° C. for 3 hours.

[7] Preparation of Anti-Bcsc-1 Antibody

Bcsc-1 introduced pET-28 a vector was expressed in *Escherichia coli* as a fusion protein with His-tag. The fusion protein was purified on a nickel chelate column, and a rabbit was immunized with the purified protein in a usual manner, to prepare an antiserum, namely, anti-Bcsc-1 polyclonal antibody. Introduction of Bcsc-1 to pET-28 a vector was carried out as follows. EcoRI and XhoI restriction fragments were introduced to Bcsc-1, and after treated with XhoI and EcoRI, the Bcsc-1 was inserted to pET-28 a vector which was also treated with XhoI and EcoRI. The introduction of EcoRI and XhoI restriction fragments to Bcsc-1 were carried out by PCR amplification using tcagGAATTCatggaggag-gctct (SEQ ID No. 5) as 5' EcoRI primer and ggtaCTC-GAGaaaggcaaagatagc (SEQ ID No. 6) as 3' XhoI primer.

[8] Cell Staining and Western Blot

The BHK cells obtained in the above [6] (which were expressed by insertion of Bcsc-1 gene) were cultured overnight in 10% FCS DMEM containing 500 ig/mL of G418 to separate the culture. The anti-Bcsc-1 polyclonal antibody (diluted 1:10$^3$) obtained in the above [7] was placed on the culture, which was then reacted at 37° C. for 1 hour, and rinsed with PBS. Further added with FITC labeled anti-rabbit IgG (H+L) (Medical & Biological Laboratories Co., Ltd.) (diluted 1:100), the culture was reacted at 37° C. for 1 hour to observe localization within the cells by a fluorescence microscope.

Also, protein recognized by this anti-Bcsc-1 polyclonal antibody was searched by Western blot, using mast cell extract, Bcsc-1 introduced BHK cell extract, extract of eosinophil in which differentiation was induced using IL-5, peripheral blood cell extract, extract of HL-60, that is, a peripheral blood system cell line, and extract of eosinophil differentiated from HL-60, as antigens.

As a result, when the mast cell extract was stained, diffuse fluorescence was recognized in the whole cytoplasma. Accordingly, it seemed that the Bcsc-1 gene is not against the mast cell surface antigen. In Western blot, when the Bcsc-1 introduced BHK cells were antigens, a band was detected at around 45 kD, which was substantially coincided with molecular weight expected from the inserted Bcsc-1. On the other hand, when the mast cell was the antigen, a band was recognized at around 90 kD. The difference in the results between 2 cell extracts gives support to a fact that the Bcsc-1 gene is not against the mast cell surface antigen.

[9] Determination of Base Sequence

The gene sequence found by the present inventors was compared with that of Bcsc-1 (SEQ ID NO. 8) stored in the database (FIG. 2). As a result, the base sequence obtained by the present inventors had one extra base A (943 in FIG. 2 or 943 of SEQ ID NO. 2) around 140 bp upstream of the initiation codon (ATG of 1055–1057 in FIG. 2) of Bcsc-1. Accordingly, it became apparent that the initiation codon of the base sequence obtained by the present inventors (36–38 in FIG. 2 or 36–38 of SEQ ID NO. 2) is located around 1000 bp upstream of the Bcsc-1 initiation codon. Furthermore, the region containing a newly found initiation codon was a typical transcription initiation sequence (ACCATGG). The protein coded by the base sequence obtained by the present inventors (SEQ ID NO. 2) was named MASA-1.

[10] Introduction of MASA-1 to BHK cells

Transfection of the BHK cells by MASA-1 was carried out in the same manner as in the above [6]. However, tcttgcCTCGAGatggtgcacttctgtgg (SEQ ID NO. 7) was used as 5' XhoI primer.

[11] Determination of MASA-1 Properties

Using the MASA-1 introduced BHK cells instead of the Bcsc-1 introduced BHK cells, cell staining and Western blot were performed in the similar way to the above [8]. However, in cell staining, a monoclonal antibody 5C12 produced by a below mentioned hybridoma ahMC5C12 was used as a primary antibody. As a result, a band at around 90 kD was observed by Western blot using the MASA-1 introduced BHK cells as an antigen, as in the case of using the mast cells, and cell surface expression was observed as well by cell staining. Expression in RBL-2H3 rat mast cells was also observed. However, no expression was observed in cord blood, eosinophil, peripheral blood lymphocyte (PBL), and HL-60 peripheral blood cell line. From the above, it was confirmed that the protein coded by MASA-1 is a mast cell surface specific protein.

[12] Hybridoma ahMC5C12 (Accession No. FERM BP-6070)

Here, as an example, a method for preparing the hybridoma ahMC5C12 is explained. Firstly, the cells obtained from cord blood cells cultured for 2 weeks in Embodiment 1 ($10^6$ cells/0.10 ml) was injected into the abdominal cavity of an infant rat 4 days after birth to ablate the induction ability of antibody production for all antigens in the cells. Then, 1.5 months later, the rat was injected to its abdominal cavity with both the MC-TC ($10^6$ cells/0.10 ml) obtained in the above [1] and complete adjuvant for immunization. Further, the rat was injected to its abdominal cavity with the cells alone 2 times every 2 weeks. The spleen was taken out 4 days after the final immunization and the cell fusion was carried out as follows.

Spleen cells taken out from the rat and myeloma cells of a mouse were mixed in a ratio of 10:1, and added with 50% polyethylene glycol 1500 as a fusion accelerator to carry out cell fusion. After the cell fusion, the cells were suspended in HAT medium containing 10% bovine serum in such a way that the cell concentration for a spleen cell becomes $5\sim10^5$ cells/ml, and distributed to a 96 well microtiter plate (Nalge Nunc International) by 200 ìl for every well. The hybridomas were cultured in a $CO_2$ incubator (5% $CO_2$, 37), and grown in HAT medium. Screening of the hybridomas of spleen cells and myeloma cells was carried out. The cells were then adapted and cultured in IMDM (Iscove's modified Dulbecco's medium) supplemented with 10% FCS (Fetal Calf Serum). Among antibodies in the culture supernatant of the hybridomas, by using MC-TC separated from skin lesion of mastocytoma as antigens, clones which produce antibodies specific to the antigens were separated by the fluorescent antibody method and named ahMC5C12 (FERM BP-6070). The harvested clone cells were suspended in 90% bovine serum containing 10% DMSO and kept in liquid nitrogen. The monoclonal antibodies, specific to mast cell surface antigens produced by the clones, were harvested by growing the ahMC5C12 in the abdominal cavity of a nude mouse and purifying the antibodies.

INDUSTRIAL AVAILABILITY

It is possible to make clear the role of the mast cells in development of allergic diseases since the present invention identifies the amino acid sequence of a mast cell surface antigen. Furthermore, since use of an antibody to the mast cell surface antigen of the present invention allows us to specifically remove or eliminate the mast cells, treatment of allergic diseases becomes possible.

Depositary Institution

Hybridoma ahMC5C12 has been deposited with the following international depositary institution, under the following accession number and deposit date.
Name: National Institute of Bioscience and Human-Technology, Agency of Industrial Science and Technology, Ministry of International Trade and Industry
Address: 1-3, Higashi 1-home, Tsukuba city, Ibaraki pref., Japan
(Zip Code 305-0046)
Accession Number and Deposit Date:
(1) hybridoma ahMC5C12
FERM BP-6070: Aug. 21, 1997

---

SEQUENCE LISTING

<160> NUMBER OF SEQ ID NOS: 7

<210> SEQ ID NO 1
<211> LENGTH: 786
<212> TYPE: PRT
<213> ORGANISM: human

<400> SEQUENCE: 1

```
Met Val His Phe Cys Gly Leu Leu Thr Leu His Arg Glu Pro Val
  1               5                  10                  15

Pro Leu Lys Ser Ile Ser Val Ser Val Asn Ile Tyr Glu Phe Val
                 20                  25                  30

Ala Gly Val Ser Ala Thr Leu Asn Tyr Glu Asn Glu Glu Lys Val
                 35                  40                  45

Pro Leu Glu Ala Phe Phe Val Phe Pro Met Asp Glu Asp Ser Ala
                 50                  55                  60

Val Tyr Ser Phe Glu Ala Leu Val Asp Gly Lys Lys Ile Val Ala
                 65                  70                  75

Glu Leu Gln Asp Lys Met Lys Ala Arg Thr Asn Tyr Glu Lys Ala
                 80                  85                  90

Ile Ser Gln Gly His Gln Ala Phe Leu Leu Glu Gly Asp Ser Ser
                 95                 100                 105

Ser Arg Asp Val Phe Ser Cys Asn Val Gly Asn Leu Gln Pro Gly
                110                 115                 120

Ser Lys Ala Ala Val Thr Leu Lys Tyr Val Gln Glu Leu Pro Leu
                125                 130                 135
```

-continued

```
Glu Ala Asp Gly Ala Leu Arg Phe Val Leu Pro Ala Val Leu Asn
            140                 145                 150

Pro Arg Tyr Gln Phe Ser Gly Ser Ser Lys Asp Ser Cys Leu Asn
            155                 160                 165

Val Lys Thr Pro Ile Val Pro Val Glu Asp Leu Pro Tyr Thr Leu
            170                 175                 180

Ser Met Val Ala Thr Ile Asp Ser Gln His Gly Ile Glu Lys Val
            185                 190                 195

Gln Ser Asn Cys Pro Leu Ser Pro Thr Glu Tyr Leu Gly Glu Asp
            200                 205                 210

Lys Thr Ser Ala Gln Val Ser Leu Ala Ala Gly His Lys Phe Asp
            215                 220                 225

Arg Asp Val Glu Leu Leu Ile Tyr Tyr Asn Glu Val His Thr Pro
            230                 235                 240

Ser Val Val Leu Glu Met Gly Met Pro Asn Met Lys Pro Gly His
            245                 250                 255

Leu Met Gly Asp Pro Ser Ala Met Val Ser Phe Tyr Pro Asn Ile
            260                 265                 270

Pro Glu Asp Gln Pro Ser Asn Thr Cys Gly Glu Phe Ile Phe Leu
            275                 280                 285

Met Asp Arg Ser Gly Ser Met Gln Ser Pro Met Ser Ser Gln Asp
            290                 295                 300

Thr Ser Gln Leu Arg Ile Gln Ala Ala Lys Glu Thr Leu Ile Leu
            305                 310                 315

Leu Leu Lys Ser Leu Pro Ile Gly Cys Tyr Phe Asn Ile Tyr Gly
            320                 325                 330

Phe Gly Ser Ser Tyr Glu Ala Cys Phe Pro Glu Ser Val Lys Tyr
            335                 340                 345

Thr Gln Gln Thr Met Glu Glu Ala Leu Gly Arg Val Lys Leu Met
            350                 355                 360

Gln Ala Asp Leu Gly Gly Thr Glu Ile Leu Ala Pro Leu Gln Asn
            365                 370                 375

Ile Tyr Arg Gly Pro Ser Ile Pro Gly His Pro Leu Gln Leu Phe
            380                 385                 390

Val Phe Thr Asp Gly Glu Val Thr Asp Thr Phe Ser Val Ile Lys
            395                 400                 405

Glu Val Arg Ile Asn Arg Gln Lys His Arg Cys Phe Ser Phe Gly
            410                 415                 420

Ile Gly Glu Gly Thr Ser Thr Ser Leu Ile Lys Gly Ile Ala Arg
            425                 430                 435

Ala Ser Gly Gly Thr Ser Glu Phe Ile Thr Gly Lys Asp Arg Met
            440                 445                 450

Gln Ser Lys Ala Leu Arg Thr Leu Lys Arg Ser Leu Gln Pro Val
            455                 460                 465

Val Glu Asp Val Ser Leu Ser Trp His Leu Pro Pro Gly Leu Ser
            470                 475                 480

Ala Lys Met Leu Ser Pro Glu Gln Thr Val Ile Phe Arg Gly Gln
            485                 490                 495

Arg Leu Ile Ser Tyr Ala Gln Leu Thr Gly Arg Met Pro Ala Ala
            500                 505                 510

Glu Thr Thr Gly Glu Val Cys Leu Lys Tyr Thr Leu Gln Gly Lys
            515                 520                 525
```

-continued

| | | | | | | | | | |
|---|---|---|---|---|---|---|---|---|---|
| Thr | Phe | Glu | Asp | Lys | Val | Thr | Phe | Pro | Leu | Gln | Pro | Lys | Pro | Asp |
| | | | | 530 | | | | | 535 | | | | | 540 |

Thr Phe Glu Asp Lys Val Thr Phe Pro Leu Gln Pro Lys Pro Asp
                530                 535                 540

Val Asn Leu Thr Ile His Arg Leu Ala Ala Lys Ser Leu Leu Gln
                545                 550                 555

Thr Lys Asp Met Gly Leu Arg Glu Thr Pro Ala Ser Asp Lys Lys
                560                 565                 570

Asp Ala Leu Asn Leu Ser Leu Glu Ser Gly Val Ile Ser Ser Phe
                575                 580                 585

Thr Ala Phe Ile Ala Ile Asn Lys Glu Leu Asn Lys Pro Val Gln
                590                 595                 600

Gly Pro Leu Ala His Arg Asp Val Pro Arg Pro Ile Leu Leu Gly
                605                 610                 615

Ala Ser Ala Pro Leu Lys Ile Lys Cys Gln Ser Gly Phe Arg Lys
                620                 625                 630

Ala Leu His Ser Asp Arg Pro Pro Ser Ala Ser Gln Pro Arg Gly
                635                 640                 645

Glu Leu Met Cys Tyr Lys Ala Lys Thr Phe Gln Met Asp Asp Tyr
                650                 655                 660

Ser Leu Cys Gly Leu Ile Ser His Lys Asp Gln His Ser Pro Gly
                665                 670                 675

Phe Gly Glu Asn His Leu Val Gln Leu Ile Tyr His Gln Asn Ala
                680                 685                 690

Asn Gly Ser Trp Asp Leu Asn Glu Asp Leu Ala Lys Ile Leu Gly
                695                 700                 705

Met Ser Leu Glu Glu Ile Met Ala Ala Gln Pro Ala Glu Leu Val
                710                 715                 720

Asp Ser Ser Gly Trp Ala Thr Ile Leu Ala Val Ile Trp Leu His
                725                 730                 735

Ser Asn Gly Lys Asp Leu Lys Cys Glu Trp Glu Leu Leu Glu Arg
                740                 745                 750

Lys Ala Val Ala Trp Met Arg Ala His Ala Gly Ser Thr Met Pro
                755                 760                 765

Ser Val Val Lys Ala Ala Ile Thr Phe Leu Lys Ser Ser Val Asp
                770                 775                 780

Pro Ala Ile Phe Ala Phe
                785

<210> SEQ ID NO 2
<211> LENGTH: 2571
<212> TYPE: DNA
<213> ORGANISM: human
<220> FEATURE:
<221> NAME/KEY: unsure
<222> LOCATION: 2484
<223> OTHER INFORMATION: n=t or a

<400> SEQUENCE: 2
ccgggctgca ggagaggaga aaatcttgca tcaccatggt gcacttctgt ggcctactca      60
ccctccaccg ggagccagtg ccgctgaaga gtatctctgt gagcgtgaac atttacgagt     120
ttgtggctgg tgtgtctgca actttgaact acgagaatga ggagaaagtt cctttggagg     180 ccttcttgt gttccccatg gatgaagact ctgctgttta cagctttgag gccttggtgg     240
atgggaagaa aattgtagca gaattacaag acaagatgaa ggcccgcacc aactatgaga     300
aagccatctc ccagggccac caggccttct tattggaggg ggacagcagc tccaggatg     360 tcttctcttg caatgtgggt aacctccaac ctgggtcgaa ggcggcagtc accctgaagt     420

-continued

```
atgtgcagga gctgcctctg gaagcagatg gggctctgcg ctttgtgctc ccagctgtcc    480
tgaatcctag ataccagttc tctgggtcgt ctaaggacag ttgccttaat gtgaagactc    540
ctatagtccc tgtggaggac ctgccctaca cactcagcat ggtcgccacc atagattccc    600
agcatggcat tgagaaggtc caatccaact gccccttgag tcctaccgag tacctaggag    660
aggacaagac ttctgctcag gtttccctgg ctgctggaca caagtttgat cgggacgtgg    720
aactcctgat ttactacaat gaggtgcata cccccagcgt ggttttggag atggggatgc    780
ctaacatgaa gccaggtcat ttgatgggag atccatctgc aatggtgagt ttctatccaa    840
atatcccaga agatcaacca tcaaatacct gtggagagtt tatctttctc atggaccgct    900
cgggaagtat gcagagcccc atgagtagcc aggatacatc tcagctgcga atacaggcag    960
ccaaggaaac actgattttg ctgctgaaga gtttacctat aggctgttat ttcaacatct   1020
atggatttgg ctcttcctat gaggcatgct ttccggagag tgtgaagtac actcagcaaa   1080
caatggagga ggctctgggg agagtgaagc ttatgcaggc cgacctaggg ggcactgaaa   1140
tcttggcacc actccagaac atttacaggg gaccctccat cccaggccac ccctacagc    1200
tttttgtctt tacagatgga gaagttcag acacgtttag tgtaattaaa gaagttagga    1260
tcaacagaca gaaacacagg tgtttctcat ttggtattgg agaaggcacc tccaccagcc   1320
taataaaagg tattgcccgg gcatcagggg gcacctcaga atttatcaca ggcaaagaca   1380
ggatgcagtc caaggctctc aggactctga acgctctct gcagcctgtg gtagaggatg   1440
tctctctgag ctggcatttg cctcctggtc tgtctgctaa aatgctttcc ccagaacaga   1500
ctgtcatctt tagggtcag agattaatca gctatgccca gctgaccggg aggatgccag   1560
cagcagagac aacaggagaa gtatgcctca aatatacact ccagggcaag acttttgagg   1620
ataaggtgac atttcctcta caacccaagc ctgatgtcaa cctcaccatt caccgccttg   1680
ctgccaagtc cttgctccag accaaggaca tgggcctcag ggagactcca gcaagtgata   1740
aaaaagatgc attgaacctt agccttgagt ctggtgtcat aagctccttc acagctttca   1800
ttgctatcaa taaggagctc aacaagccgg ttcaggggcc tctggctcat agggacgtcc   1860
caaggccaat tctgttgggt gcttctgccc cattgaagat aaaatgccaa tcaggttttc   1920
gaaaggcctt acactctgac cgtcctcctt ctgcatctca gcccagaggg gaacttatgt   1980
gttataaggc caagacattc cagatggacg attacagtct ctgtgggttg ataagtcaca   2040
aggaccagca cagtccaggc tttgagaga tcaccttgt gcagctgatt taccaccaaa   2100
atgcaaatgg ttcctgggat ctgaatgaag atctagccaa gatcctaggt atgagtttgg   2160
aagaaataat ggctgcacag cctgccgagc ttgtggattc ctcaggctgg gccaccatcc   2220
tggccgtgat ctggctgcac agcaatggta aggacttgaa gtgtgaatgg gagcttctgg   2280
aaaggaaggc cgtggcctgg atgcgtgccc atgcaggctc caccatgcct tcggttgtga   2340
aagctgctat tactttcctg aagtcatctg tggatcctgc tatctttgcc ttttgaagat   2400
accatccaga aaaagaagtg cctttaattt gctactgtca tttcctctag tatcactttt   2460
gctgtgatga tgtgttcttg tgtnttataa ctctttattt tttgccataa agtaaagga    2520
tgcttactcc acttcgaaaa aaaaaaaaaa aaaaaaaaa aaaaaaaaa a               2571
```

<210> SEQ ID NO 3
<211> LENGTH: 27
<212> TYPE: DNA
<213> ORGANISM: Artificial Sequence
<220> FEATURE:
<223> OTHER INFORMATION: primer -continued

```
<400> SEQUENCE: 3
cagctcgaga tggaggaggc tctgggg                                           27

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
tctggatgcg gccgctcaaa ggcaaagat                                         29

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
tcaggaattc atggaggagg ctct                                              24

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
ggtactcgag aaaggcaaag atagc                                             25

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
tcttgcctcg agatggtgca cttctgtgg                                         29
```

What is claimed is:

1. An isolated mast cell surface antigen comprising the amino acid sequence listed in SEQ ID NO. 1.

* * * * *

UNITED STATES PATENT AND TRADEMARK OFFICE
CERTIFICATE OF CORRECTION

PATENT NO. : 7,045,597 B2  Page 1 of 2
APPLICATION NO. : 10/250644
DATED : May 16, 2006
INVENTOR(S) : Makoto Kawai et al.

It is certified that error appears in the above-identified patent and that said Letters Patent is hereby corrected as shown below:

Column 2, line 51, change "50 iM" to --50 µM--.

Column 2, line 52, change "50 ig/ml" to --50 µg/ml--.

Column 3, line 43, change "400 iL" to --400 µL--.

Column 3, line 45, change "800 iL" to --800 µL--.

Column 3, line 60, change "300 iL" to --300 µL--.

Column 3, line 63, change "500 iL" to --500 µL--.

Column 3, line 65, change "200 iL" to --200 µL--.

Column 3, line 66, change "10 iL" to --10 µL--.

Column 3, line 66, change "400 iL" to --400 µL--.

Column 4, line 15, change "100 iL" to --100 µL--.

Column 4, line 15, change "500 iL" to --500 µL--.

Column 4, line 54, (both occurences) change "50 iL" to --50 µL--.

Column 4, line 55, change "80 iL" to --80 µL--.

Column 5, line 46, change "100 iL" to --100 µL--.

Column 5, line 47, change "2.5 iL(2.5 ig)" to --2.5 µL (2.5 µg)--.

Column 5, line 48, change "200 iL" to --200 µL--.

Column 5, line 48, change "100 iL" to --100 µL--.

Column 5, line 50, change "800 iL" to --800 µL--.

Column 6, line 4, change "500 ig/mL" to --500 µg/mL--.

Column 7, line 21, change "5~$10^5$" to --5 x $10^5$--.

UNITED STATES PATENT AND TRADEMARK OFFICE
CERTIFICATE OF CORRECTION

PATENT NO. : 7,045,597 B2
APPLICATION NO. : 10/250644
DATED : May 16, 2006
INVENTOR(S) : Makoto Kawai et al.

It is certified that error appears in the above-identified patent and that said Letters Patent is hereby corrected as shown below:

Column 7, line 23, change "200 il" to --200 µL--.

Column 7, line 24, change "37)" to --37°C)--.

Signed and Sealed this

Sixth Day of March, 2007

JON W. DUDAS
*Director of the United States Patent and Trademark Office*